US011198658B2

(12) United States Patent
Richardson et al.

(10) Patent No.: US 11,198,658 B2
(45) Date of Patent: Dec. 14, 2021

(54) PROCESS FOR THE OLIGOMERIZATION OF OLEFINS

(71) Applicant: TOTAL MARKETING SERVICES, Puteaux (FR)

(72) Inventors: Christine-Joy Richardson, King of Prussia, PA (US); Laurent Germanaud, Saint Alyre d'Arlanc (FR); Stéphane Kressmann, Communay (FR)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

(21) Appl. No.: 16/969,297

(22) PCT Filed: Mar. 15, 2019

(86) PCT No.: PCT/EP2019/056532
§ 371 (c)(1),
(2) Date: Aug. 12, 2020

(87) PCT Pub. No.: WO2019/175377
PCT Pub. Date: Sep. 19, 2019

(65) Prior Publication Data
US 2021/0024437 A1 Jan. 28, 2021

(30) Foreign Application Priority Data

Mar. 16, 2018 (EP) .................................. 18305298
Feb. 11, 2019 (EP) .................................. 19305166

(51) Int. Cl.
*C07C 2/12* (2006.01)
*C07C 1/24* (2006.01)
*C07C 11/08* (2006.01)

(52) U.S. Cl.
CPC ................. *C07C 2/12* (2013.01); *C07C 1/24* (2013.01); *C07C 11/08* (2013.01); *C07C 2521/12* (2013.01); *C07C 2529/06* (2013.01)

(58) Field of Classification Search
CPC .. C07C 1/24; C07C 2/08; C07C 11/02; C07C 11/10; C07C 11/08; C07C 2521/12; C07C 2529/06; C07C 2529/65; C07C 2/12; C10G 2300/1011; C10G 2300/1088; C10G 2400/10; C10G 2400/18; C10G 50/02
See application file for complete search history.

(56) References Cited

U.S. PATENT DOCUMENTS

| 5,008,466 A * | 4/1991 | Schleppinghoff ......... C07C 2/28 568/697 |
|---|---|---|
| 2011/0301316 A1 | 12/2011 | Dubois |
| 2013/0180884 A1 | 7/2013 | Minoux et al. |
| 2016/0221894 A1 * | 8/2016 | Xu .......................... C10G 45/36 |

OTHER PUBLICATIONS

International Search Report and Written Opinion of the International Searching Authority, for International Application No. PCT/EP2019/056532, dated May 27, 2019.
Vidal et al., "Biosynthesis of higher alcohol flavour compounds by the yeast *Saccharomyces cerevisiae*: Impact of oxygen availability and responses to glucose pulse in minimal growth medium with leucine as sole nitrogen source", Yeast, 2015, vol. 32, pp. 47-56.
Yuan et al., "Engineering the leucine biosynthetic pathway for isoamyl alcohol overproduction in *Saccharomyces cerevisise*", J Ind Microbiol Biotechnol, vol. 44, No. 1, Jan. 2017, 16 pages, abstract provided only.

\* cited by examiner

*Primary Examiner* — Sharon Pregler
(74) *Attorney, Agent, or Firm* — Birch, Stewart, Kolasch & Birch, LLP

(57) ABSTRACT

A process for preparing a hydrocarbon fluid includes a step of oligomerising an initial hydrocarbon composition which contains, in relation to the total weight of said initial hydrocarbon composition, at least 2% by weight of 3-methyl-but-1-ene, at least 5% by weight of 2-methyl-but-2-ene and at least 5% by weight of 2-methyl-but-1-ene.

20 Claims, No Drawings

PROCESS FOR THE OLIGOMERIZATION OF OLEFINS

FIELD OF THE INVENTION

The present invention concerns a process for oligomerizing olefins affording good yields and good selectivity, for varied applications and in particular as solvent fluids and jet fuel.

TECHNICAL BACKGROUND OF THE INVENTION

Hydrocarbon fluids are widely used as solvents, for example in adhesives, cleaning liquids, explosives, solvents for decorative coatings and printing inks, light oils used in applications such as extraction of metals, metal working or mould release, industrial lubricants and drilling fluids. Hydrocarbon fluids can also be employed as diluting oils in adhesives and sealing systems such as silicone mastics, as viscosity reducers in formulations containing plasticized polyvinyl chloride, as carriers in polymer formulations used as flocculants e.g. for water treatment, in mining operations or the paper industry and also as thickeners for print pastes. Hydrocarbon fluids can further be used as solvents in a broad range of other applications e.g. in chemical reactions.

The chemical nature and composition of hydrocarbon fluids vary considerably depending on the intended use of the fluid. Major properties of hydrocarbon fluids are the following: distillation curve (generally determined in accordance with ASTM D86 or ASTM D1160 methods using the vacuum distillation technique employed for heavier materials), flash point, density, aniline point (determined in accordance with the ASTM D611 method), aromatic content, sulfur content, viscosity, colour and refractive index. These fluids can be classified as paraffinic, isoparaffinic, dearomatized, naphthenic, non-dearomatized and aromatic.

Document U.S. Pat. No. 5,008,466 discloses an isomerization process of alkenes having a terminal double bond to obtain alkenes having an internal double bond. This document does not disclose a process for oligomerizing branched C5 olefins.

SUMMARY OF THE INVENTION

These objectives are reached with a novel process for the oligomerization of olefins.

The invention concerns a process for preparing a hydrocarbon fluid, comprising an oligomerization step of an initial hydrocarbon composition comprising at least 2% wt. of 3-methyl-but-1-ene, at least 5% wt. of 2-methyl-but-2-ene and at least 5% wt. of 2-methyl-but-1-ene relative to the total weight of the initial hydrocarbon composition.

In one embodiment of the invention, the initial hydrocarbon composition is derived from biomass.

In one embodiment of the invention, the initial hydrocarbon composition is obtained via dehydration of alcohol(s), preferably via dehydration of fusel oil.

In one embodiment of the invention, the initial hydrocarbon composition comprises at least 20% wt., preferably at least 30% wt., more preferably at least 40% wt., further preferably at least 50% wt., still further preferably at least 60% wt. of branched olefins having 5 carbon atoms selected from among 3-methyl-but-1-ene, 2-methyl-but-2-ene and 2-methyl-but-1-ene, relative to the total weight of the initial composition.

In one embodiment of the invention, the initial hydrocarbon composition comprises at least 20% wt., preferably at least 30% wt., more preferably at least 40% wt., further preferably at least 50% wt., still further preferably at least 60% wt. of 2-methyl-but-2-ene, relative to the total weight of the composition.

In one embodiment of the invention, the initial hydrocarbon composition comprises 3-methyl-but-1-ene in a weight proportion such that the 3-methyl-but-1-ene represents the olefin having 5 carbon atoms present in majority amount in the initial hydrocarbon composition.

In one embodiment of the invention, the oligomerization step is conducted in the presence of a catalyst selected from among alumina and aluminosilicates.

In one embodiment of the invention, the catalyst is an aluminosilicate and the $SiO_2/Al_2O_3$ molar ratio of the catalyst ranges from 10 to 80, preferably from 15 to 50.

In one embodiment of the invention, the catalyst is a mesoporous aluminosilicate having a BET specific surface area greater than or equal to 50 $m^2/g$, preferably ranging from 150 to 1200 $m^2/g$, preferably ranging from 250 to 550 $m^2/g$.

In another embodiment of the invention, the catalyst is an amorphous Si Al catalyst (ASA) and has content of 5 to 95% wt. of silica ($SiO_2$), a BET specific surface area ranging from 100 to 550 $m^2/g$ and accessible pore size ranging from 2 to 14 nm.

In one embodiment, the process of the invention is implemented at a temperature ranging from 80 to 220° C., preferably from 90 to 210° C., more preferably from 100 to 200° C.

In one embodiment, the process of the invention is implemented at a pressure ranging from 2 to 50 bars, preferably 5 to 40 bars, more preferably 10 to 30 bars.

In one embodiment, the process of the invention further comprises at least one treatment step, preferably a hydrogenation step and/or fractionation step.

In one embodiment, the process of the invention comprises a step to recycle an effluent comprising non-reacted C5 olefins.

The invention also concerns a hydrocarbon fluid capable of being obtained with the process of the invention.

Finally, the invention concerns the use of the hydrocarbon fluid of the invention as crude or hydrogenated and/or fractionated solvent cut for the formulation of inks, paints, varnishes, cleaning products, lubricants for metal working, dielectric fluids, drilling fluids, cosmetic products.

With the process of the invention, it is possible to obtain a mixture of hydrocarbon fluids with good yields and good selectivity.

The process of the invention can be implemented from raw material of biological origin.

The process of the invention allows various hydrocarbon fractions to be obtained using a single oligomerization step optionally followed by a hydrogenation and/or fractionation step.

DETAILED DESCRIPTION OF THE INVENTION

The invention concerns a process for preparing a hydrocarbon fluid, comprising an oligomerization step of an initial hydrocarbon composition comprising at least 2% wt. of 3-methyl-but-1-ene, at least 5% wt. of 2-methyl-but-2-ene and at least 5% wt. of 2-methyl-but-1-ene relative to the total weight of the hydrocarbon composition.

Initial Hydrocarbon Composition (Called «Initial Composition»)

The initial composition (which undergoes oligomerization) comprises three different branched olefins each having 5 carbon atoms. In particular, the initial composition comprises at least 2% wt. of 3-methyl-but-1-ene, at least 5% wt. of 2-methyl-but-2-ene and at least 5% wt. of 2-methyl-but-1-ene relative to the total weight of the initial composition.

By «branched olefin having 5 carbon atoms», it is meant an olefin comprising a branched hydrocarbon chain with 5 carbon atoms. In the meaning of the present invention, the expression «branched C5 olefin» designates a branched olefin having 5 carbon atoms.

In one embodiment, the initial composition comprises at least 20% wt., preferably at least 30% wt., more preferably at least 40% wt., further preferably at least 50% wt., still further preferably at least 60% wt. of branched olefins having 5 carbon atoms, relative to the total weight of the initial composition, selected from among 3-methyl-but-1-ene, 2-methyl-but-2-ene and 2-methyl-but-1-ene.

In one particular embodiment, the initial composition comprises at least 20% wt., preferably at least 30% wt., more preferably at least 40% wt., further preferably at least 50% wt., still further preferably at least 60% wt. of 2-methyl-but-2-ene, relative to the total weight of the initial composition.

In one embodiment of the invention, the initial composition comprises between 50 and 90% wt. of 2-methyl-but-2-ene, relative to the total weight of olefins having 5 carbon atoms, preferably between 55 and 80% wt.

In another embodiment of the invention, the initial hydrocarbon composition comprises 3-methyl-but-1-ene in a weight proportion such that the 3-methyl-but-1-ene represents the olefin having 5 carbon atoms present in majority amount in the initial hydrocarbon composition. Therefore, preferably, the initial composition has a weight ratio of (3-methyl-but-1-ene)/(each C5 olefin other than 3-methyl-but-1-ene) higher than or equal to 1, preferably strictly higher than 1, more preferably higher than or equal to 1.2, further preferably higher than or equal to 1.5.

In one particular embodiment of the invention, the initial composition comprises at least 50% wt. of 3-methyl-but-1-ene, relative to the total weight of olefins having 5 carbon atoms.

In one embodiment of the invention, the initial composition is derived from conversion of biomass. By derived from the conversion of biomass, it is meant a composition produced from raw materials of biological origin preferably selected from among sugars and sugar precursors such as cellulose, hemicellulose, lignocellulose and mixtures thereof, these latter possibly being produced from microorganisms such as yeasts, algae and bacteria.

In particular, the initial composition can be obtained via dehydration of alcohol(s), preferably alcohol(s) derived from the conversion of biomass. Some yeasts can produce the preferred alcohols in majority amount as shown in the work by the teams of Esteban Espinosa Vidal, Marcos Antonio de Morais Jr, Jean Marie Francois and Gustavo M. de Billerbeck published in the journal Yeast 2015; 32: 47-56: "Biosynthesis of higher alcohol flavour compounds by the yeast *Saccharomyces cerevisiae*: impact of oxygen availability and responses to glucose pulse in minimal growth medium with leucine as sole nitrogen source" or in the work by the team Yuan J, Mishra P and Ching C B "Engineering the leucine biosynthetic pathway for isoamyl alcohol overproduction in *Saccharomyces cerevisiae*" published in the journal J Ind Microbiol Biotechnol. 2017 January; 44(1): 107-117.

In one preferred embodiment, the initial composition is obtained by dehydration of fusel oil. By «fusel oil», it is meant a mixture of alcohols derived from fermentation of raw material of biological origin followed by distillation of the effluent obtained after fermentation. Fusel oil is well known to persons skilled in the art as by-product of alcoholic fermentation. Fusel alcohols are a mixture of alcohols such as propanol, butanol, isobutanol, pentanol, methylbutanols, hexanol, fatty alcohols, terpenes and furfural. They are formed via alcoholic fermentation as metabolism by-products. The main compounds contained in so-called fusel alcohols are: propanol, butanols, amyl alcohol, isoamyl alcohols and hexanol. Fusel oil may optionally comprise heavier linear alcohols e.g. C7 and/or C8. These products are formed during fermentation when temperature and pH are high. They are concentrated in distillation tails at the end of the process. They then have an oily appearance, hence their name fusel oil. Fusel oil may optionally also comprise ethanol depending upon the quality of separation after fermentation.

Fusel oil can be obtained by different processes well known to skilled persons e.g. via direct sampling in the distillation column followed by cooling. The sample can optionally be purified e.g. via extraction followed by decanting. Liquid/liquid extraction through the addition of water followed by decanting allows two phases to be obtained. The top phase essentially contains amyl and butyl alcohols that are scarcely water-soluble. It is called decanted or crude fusel oil. It can be chemically treated (in general with a salt-saturated solution) and/or fractionated via distillation to remove the water content and to separate residual ethanol. A «refined» fusel oil is then obtained. Other purification methods of fusel oil use adsorbents that are regenerated to separate the different fractions. Among the numerous tested adsorbents, granular activated plant carbon is preferred since it can adsorb eight times its weight of fusel oil. The alcohols can be then be isolated from the other constituents via a fractionation step.

In one embodiment, the initial composition is obtained via dehydration of a mixture comprising at least 12% wt. of alcohols having 5 carbon atoms, at least 1% wt. of ethanol, less than 5% wt. of ester(s) and less than 5% wt. of water, relative to the total weight of the mixture. In one particular embodiment, the initial composition is obtained by dehydrating a mixture comprising at least 20% wt., preferably at least 30% wt., more preferably at least 40% wt., further preferably at least 50% wt., still further preferably at least 60% wt. of alcohols having 5 carbon atoms, relative to the total weight of the mixture.

Preferably the alcohol(s) having 5 carbon atoms contained in the mixture are selected from among C5 isoamyl iso-alcohols, preferably from among 3-methyl-butan-1-ol, 2-methyl-butan-1-ol and mixtures thereof. By C5 iso-alcohols, it is meant an alcohol with a branched hydrocarbon chain having 5 carbon atoms.

In the present invention, the alcohols are preferably primary alcohols, in other words alcohols in which the —OH function is linked to a —CH$_2$— group.

Said dehydration can be performed using a dehydration catalyst e.g. selected from among zeolites, aluminas, silica-aluminas and acid catalysts, preferably from among zeolites, aluminas and silica-aluminas. In one embodiment of the invention, the dehydration catalyst is a silica-alumina selected from among zeolites and aluminas. In another embodiment of the invention, the dehydration catalyst is an alumina. Preferably, the dehydration catalyst is selected from among γ aluminas, H-β zeolites and H-γ zeolites. These dehydration catalysts as such are well known to skilled persons and are commercially available.

In one embodiment, the catalyst for dehydration is selected from among zeolites and has a $SiO_2/Al_2O_3$ molar ratio higher than or equal to 10, preferably higher than or equal to 20, more preferably higher than or equal to 30, further preferably higher than or equal to 50, most preferably higher than or equal to 80.

In another embodiment, the catalyst for dehydration is selected from among aluminas, preferably gamma aluminas (γ alumina). As examples of catalysts of alumina type, mention can be made of catalysts in the PurAl® range marketed by Sasol.

In one advantageous embodiment, the catalyst for dehydration is a zeolite of ferrierite type e.g. in powder or extrudate form. As examples, mention can be made of CP914® in the form of zeolite ferrierite ammonium powder, or CP914® CYL 1.6, in the form of extrudates, both marketed by Zeolyst.

It is possible, between the dehydration step and oligomerization step, to make provision for a separation step to remove water-type compounds and optionally residual esters and alcohols that are present to obtain the desired initial composition for oligomerization according to the invention.

Catalyst for Oligomerization

The catalyst for oligomerization can be selected from among zeolites, aluminas, silica-aluminas and aluminosilicates. These catalysts as such are well known to skilled persons and are commercially available.

In one embodiment of the invention, the catalyst for oligomerization according to the invention has a $SiO_2/Al_2O_3$ molar ratio ranging from 10 to 80, preferably ranging from 15 to 50. In one particular embodiment of the invention, the catalyst for oligomerization is selected from among aluminosilicates. Therefore, in one particular embodiment the catalyst for oligomerization of the invention differs from a zeolite.

In one embodiment of the invention, the catalyst is selected from among aluminosilicates having a pore size ranging from 1 to 50 nm, preferably from 1 to 25 nm, more preferably from 2 to 20 nm.

In one embodiment, the catalyst of aluminosilicate type used in the invention is a mesoporous aluminosilicate typically having a BET specific surface area greater than or equal to 50 m$^2$/g, preferably ranging from 150 to 1200 m$^2$/g, more preferably ranging from 250 to 550 m$^2$/g. One example of said catalyst is a catalyst of type Al-MCM-41.

In another embodiment, the catalyst of aluminosilicate type used in the invention is an amorphous Si Al catalyst (ASA) typically having 5 to 95% wt. of silica ($SiO_2$), a BET specific surface area ranging from 100 to 550 m$^2$/g and pore size ranging from 2 to 14 nm.

In the present invention, the specific surface area is measured according to the BET method, measuring specific surface area by adsorption of a gas, a method well known to skilled persons.

In the present invention, pore size is measured by physisorption of nitrogen.

Oliqomerization

In one embodiment of the process of the invention, the initial composition (oligomerization feed) is contacted with the catalyst at a temperature ranging from 80 to 220° C., preferably from 90 to 210° C., more preferably from 100 to 200° C.

In one embodiment of the invention, the oligomerization step is implemented at a pressure ranging from 2 to 50 bars, preferably 5 to 40 bars, more preferably 10 to 30 bars.

In one embodiment of the invention, the oligomerization step is implemented at a temperature ranging from 90 to 220° C., preferably 95 to 210° C., more preferably 100 to 200° C. and at a pressure ranging from 2 to 50 bars, preferably 5 to 40 bars, more preferably 10 to 30 bars.

In one embodiment, the oligomerization process is implemented in liquid phase.

Oligomerization allows C10 dimers, C15 trimers and other molecules to be obtained such as C6-C9 molecules and C11-C14 molecules.

It is possible to provide a separation step after the oligomerization step to separate the molecules having 5 or fewer carbon atoms, used as feed, from produced molecules having 6 or more carbon atoms. This separation step therefore allows a first flow to be obtained comprising molecules having 5 or fewer carbon atoms, and a second flow comprising molecules having 6 or more carbon atoms. In this embodiment, it is possible to provide a step to recycle effluent comprising non-reacted C5 olefins. It is therefore possible to provide a recycling loop to return the first flow or all or part of the second flow upstream of the oligomerization reaction.

After the oligomerization step, the reaction product obtained can undergo different treatments. If a separation step is performed after oligomerization, subsequent treatments are preferably conducted on the second flow comprising molecules having 6 or more carbon atoms.

Among subsequent treatments, mention can be made of hydrogenation and/or fractionation.

In one embodiment, the process of the invention comprises an oligomerization step such as previously described, followed by a hydrogenation step. Hydrogenation can be performed using any method well known to skilled persons.

In one embodiment, the process of the invention comprises an oligomerization step such as previously described followed by a fractionation step.

In one embodiment, the process of the invention comprises an oligomerization step such as previously described, followed by a hydrogenation step, itself followed by a fractionation step.

Fractionation of a hydrocarbon fluid is well known to skilled persons. In particular, it allows hydrocarbon fractions to be obtained having varying distillation ranges. Therefore, the process of the invention allows a hydrocarbon fraction to be obtained defined by the distillation range thereof.

Hydrocarbon Fluid

The invention also concerns hydrocarbon fluids capable of being obtained with the preparation process of the invention.

Finally, the invention also proposes the use of the hydrocarbon fluid of the invention as crude or hydrogenated and/or fractionated solvent cut for the formulation of inks, paints, varnishes, cleaning products, lubricants for metal working, dielectric fluids, drilling fluids, cosmetic products.

EXAMPLES

In the remainder of the present description, examples are given to illustrate the present invention which are in no way intended to limit the scope thereof.

Example 1: Dehydration of a Fusel Oil

A catalyst for dehydration of fusel oil was prepared from extrudates of γ-$Al_2O_3$ having a diameter of 1.2 mm, a specific surface area of 200 $m^2$/g, a pore size distribution centred around 124 Å and pore volume of 0.588 mL/g. The extrudates were ground and screened through 35-45 mesh (0.500-0.354 μm).

A tubular reactor in stainless steel, having an inner diameter of 10 mm, was fed with 20 mL of γ-$Al_2O_3$ catalyst thus obtained. The voids either side of the catalyst were filled with powder silicon carbide (SiC) of diameter 0.5 mm.

The temperature profile was monitored with a thermocouple placed inside the reactor. The reactor temperature was increased at a rate of 60° C./h up to 550° C. under a stream of 45 NL/h nitrogen and 10 NL/h air. The temperature was held at 550° C. and the stream of nitrogen reduced to 30 NL/h. After 30 minutes, the nitrogen stream was further reduced to 10 NL/h. After an additional 30 minutes, the nitrogen stream was stopped and the air stream increased to 20 NL/h. After 1 hour, the reactor temperature was lowered to 400° C. and the reactor purged with nitrogen.

A feed of biosourced crude fusel oil containing about 20.9% wt. of ethanol, 1.5% wt. of propan-1-ol, 0.3% wt. of butan-1-ol, 14.0% wt. of isobutanol, 45.6% wt. of 3-methyl-butan-1-ol, 16.7% wt. of 2-methyl-butan-1-ol, 0.1% wt. of ethyl pentanoate, 0.3% wt. of ethyl hexanoate relative to the total weight of the feed, and higher ethyl esters and derivatives of pyrazine, was filtered to remove the fine particles.

The stream of nitrogen in the reactor was replaced by a flow of filtered fusel oil feed. The feed was directed through a pre-heater onto the catalytic bed at an initial inner temperature of the reactor of 400° C. and overall hourly volume velocity (HVV) of 4 $h^{-1}$. The temperature was increased to 425° C. The catalytic tests were performed in current downflow at a pressure of 2 barg (bar gauge, manometric pressure) over a temperature range of 300 to 450° C. and at a weight hourly space velocity (WHSV) ranging from 2 to 7 $h^{-1}$. Analysis of the products was conducted using in-line gas phase chromatography.

The results are given in Table 1 below. The values are given in weight percent relative to the total weight of the products.

TABLE 1

| Conversion of alcohols (in % wt.) | | |
|---|---|---|
| HVV ($h^{-1}$) | 4 | 4 |
| T (° C.) | 400 | 425 |
| $C_2$ (ethylene) | 16.0 | 10.4 |
| $C_3$ (propylene) | 1.3 | 0.9 |
| $C_4$ (butenes) | 12.2 | 7.3 |
| 3-methyl-but-1-ene | 33.2 | 11.9 |
| 2-methyl-but-1-ene | 8.9 | 7.9 |
| 2-methyl-but-2-ene | 21.0 | 17.9 |
| Higher olefins and others | 7.5 | 43.7 |

Full conversion of alcohols was observed at both temperatures. At 400° C., the 3-methyl-but-1-ene represents about 53% wt. of isoamylenes. By increasing the temperature to 425° C., the proportion of 2-methyl-but-2-ene among the C5 olefins increases and the total quantity of isoamylenes decreases due to the formation of heavier products.

Example 2: Dehydration of a Distilled Fusel Oil

A catalyst for dehydration of fusel oil was prepared from a zeolite of ferrierite type (Zeolyst CP914®, powder) calcined under a stream of 50 NL/h nitrogen at 550° C. for 6 hours (1° C. per minute). The catalyst was ground and screened through 35-45 mesh (0.500-0.354 μm).

A tubular reactor in stainless steel having an inner diameter of 10 mm was fed with 10 mL (5.53 g) of the ferrierite catalyst thus obtained. The voids either side of the catalyst were filled with powdered silicon carbide (SiC) of diameter 0.5 mm.

The temperature profile was monitored with a thermocouple placed inside the reactor. The temperature of the reactor was increased at a rate of 60° C./h up to 550° C. under a stream of 10 NL/h nitrogen. After hour, the temperature of the reactor was lowered to 260° C. and the reactor purged with nitrogen.

A feed of distilled, biosourced fusel oil (125-135° C. cut) was prepared containing less than 0.1% wt. of ethanol, less than 0.1% wt. of propan-1-ol, less than 0.1% wt. of butan-1-ol, about 1.0% wt. of isobutanol, 83.5% wt. of 3-methyl-butan-1-ol, 13.8% wt. of 2-methyl-butan-1-ol, less than 0.1% wt. of ethyl pentanoate relative to the total weight of the feed, and higher ethyl esters and derivatives of pyrazine.

The feed of distilled fusel oil was directed through a pre-heater onto the catalytic bed at an initial inner temperature of the reactor of 260° C., overall hourly volume velocity (HVV) of 8 h$^{-1}$ and pressure of 2 barg. The temperature was gradually increased up to 375° C.

Analysis of the products was carried out using in-line gas phase chromatography.

At 375° C., a conversion rate of isoamyl alcohol of 78% was obtained. By increasing the temperature up to 400° C., the conversion rate was higher than 99%, with 55% of 2-methyl-but-2-ene in the effluent. These operating conditions were maintained for 100 hours without significant loss of selectivity.

Example 3: Dehydration of a Distilled Fusel Oil

A catalyst for dehydration of fusel oil was prepared from a zeolite of ferrierite type (Zeolyst CP914® CYL-1.6) in the form of extrudates that were ground and screened through 35-45 mesh (0.500-0.354 μm).

A tubular reactor in stainless steel of inner diameter 10 mm, was fed with 10 mL of the ferrierite catalyst thus obtained. The voids either side of the catalyst were filled with powdered silicon carbide (SiC) of diameter 0.5 mm.

The temperature profile was monitored with a thermocouple placed inside the reactor. The temperature of the reactor was increased at a rate of 60° C./h up to 550° C. under a stream of 10 NL/h nitrogen. After 1 hour, the temperature of the reactor was lowered to 270° C. and the reactor purged with nitrogen.

A feed of distilled, biosourced fusel oil (125-135° C. cut) was prepared containing less than 0.1% wt. of ethanol, less than 0.1% wt. of propan-1-ol, less than 0.1% wt. of butan-1-ol, about 1.0% wt. of isobutanol, 83.5% wt. of 3-methyl-butan-1-ol, 13.8% wt. of 2-methyl-butan-1-ol, less than 0.1% wt. of ethyl pentanoate relative to the total weight of the feed, and higher ethyl esters and derivatives of pyrazine.

The feed of distilled fusel oil was directed through a pre-heater onto the catalytic bed at an initial inner temperature of the reactor of 270° C., overall hourly volume velocity of 8 h$^{-1}$ and pressure of 2 barg. The temperature was gradually increased up to 350° C.

Analysis of the products was carried out using in-line gas phase chromatography.

At 350° C., almost complete conversion was obtained (less than 1% alcohol) with 60% of 2-methyl-but-2-ene in the effluent. By increasing the temperature up to 360° C., 62-63% of 2-methyl-but-2-ene was obtained in the effluent. These operating conditions were maintained for 50 hours without significant loss of selectivity. By increasing the temperature up to 380° C., a slight decrease was observed in the proportion of 2-methyl-but-2-ene in the effluent and an increase in the proportions of trans-2-pentene and cis-2-pentene.

Example 4: Mixture of Isoamylene Isomers

Dehydration of fusel oil leads to the following mixture of isoamylene isomers: 3-methyl-but-1-ene (3MB1), 2-methyl-but-2-ene (2MB2) and 2-methyl-but-1-ene (2MB1). The ratio of isoamylenes depends in particular on the dehydration catalyst used, dwell time and applied temperature for the dehydration reaction.

An isoamylene mixture in a weight ratio 2MB1/3MB1/2MB2=20:10:70 was assayed under an oligomerization reaction in a double-walled tubular reactor filled with 3.0 g of amorphous Si Al catalyst and 12 g of homogeneously distributed glass beads (diameter <1 mm) to form the catalytic bed. The BET specific surface area of the amorphous silica-alumina catalyst (ASA) such as measured according to the ASTM D 4365-95 method (Reapproved 2008) ranged from 100 to 550 m$^2$/g with a pore size ranging from 2 to 14 nm.

The mixture of isoamylenes (2MB1/3MB1/2MB2=20:10:70) was fed via the cooled HPLC pump at a flow rate of 0.3 mL/min (WHSV=4 h$^{-1}$) and the reactor was gradually heated via heat-exchange fluid to reach 155° C. in the catalytic bed. The pressure was held at 25 bars in the system by means of a Kammer valve driven by a pressure sensor. Samples were taken after cooling to 0° C. at the indicated times, diluted and analysed by GC-MS.

TABLE 2

| | | | | | Results of oligomerization | | | | |
|---|---|---|---|---|---|---|---|---|---|
| | | Assayed reactant yield (RY) vs Standards (GC/MS -electronic impact)* expressed in % wt. | | | | | | | Weight |
| Conditions | Accumulated time (h) | 2MB2 | 3MB1 | 2MB1 | RY C6-C9 | RY$_{dimers}$ C10 | RY C11-C14 | RY$_{trimers}$ C15 | ratio C10/(C11-C15) |
| 155° C. 25 bars | 4 | 5 | 2 | 2 | 9 | 39 | 15 | 12 | 59/41 |

*Detection was conducted with the following standards: C15 assay vs. 1-pentadecene standard (taken at 97%, GC); C10 assay vs. 1-decene standard (taken at 98%, GC); estimated C6-C9 compounds vs. 1-decene standard; estimated C11-C14 compounds vs. pentadecene standard; Compounds >C15 non-assayed.

Table 2 shows a most satisfactory conversion rate. In addition, it was observed that C6-C9 and C11-14 compounds were obtained in non-negligible quantities, which allows hydrocarbon fluids to be obtained that are adapted to different applications.

Example 5: Other Mixture of Isoamylene Isomers

An assay was conducted with the following mixture of isoamylene isomers: 2MB1/3MB1/2MB2=14:53:33 (weight ratio) with an amorphous Si Al catalyst and identical operating mode to the one in Example 4. The following performance results were obtained:

TABLE 3

Results of oligomerization

| Conditions | Accumulated time (h) | 2MB2 | 3MB1 | 2MB1 | RR C6-C9 | $RR_{dimers}$ C10 | RR C11-C14 | $RRt_{trimers}$ C15 | Weight ratio C10/(C11-C15) |
|---|---|---|---|---|---|---|---|---|---|
| 155° C. 25 bars | 3 | 6 | 14 | 3 | 6 | 34 | 6 | 9 | 69/31 |

*Detection was conducted with the following standards: C15 assay vs. 1-pentadecene standard (taken at 97%, GC); C10 assay vs. 1-decene standard (taken at 98%, GC); estimated C6-C9 compounds vs. 1-decene standard; estimated C11-C14 compounds vs. pentadecene standard; Compounds >C15 non-assayed.

Table 3 shows a satisfactory conversion rate and non-negligible reactant yield with respect to the compounds different from the dimers (C10) and trimers (C15), i.e. C6-C9 and C11-C14 compounds.

The invention claimed is:

1. A process for preparing a hydrocarbon fluid, comprising an oligomerization step of an initial hydrocarbon composition comprising at least 2% wt. of 3-methyl-but-1-ene, at least 5% wt. of 2-methyl-but-2-ene and at least 5% wt. of 2-methyl-but-1-ene relative to the total weight of the initial hydrocarbon composition.

2. The process according to claim 1, wherein the initial hydrocarbon composition is derived from biomass.

3. The process according to claim 1, wherein the initial hydrocarbon composition is obtained via dehydration of alcohol(s).

4. The process according to claim 1, wherein the initial hydrocarbon composition comprises at least 20% wt. of branched olefins having 5 carbon atoms selected from among 3-methyl-but-1-ene, 2-methyl-but-2-ene and 2-methyl-but-1-ene, relative to the total weight of the initial composition.

5. The process according to claim 1, wherein the initial hydrocarbon composition comprises at least 20% wt. of 2-methyl-but-2-ene, relative to the total weight of the composition.

6. The process according to claim 5, wherein the initial hydrocarbon composition comprises 3-methyl-but-1-ene in a weight proportion such that the 3-methyl-but-1-ene represents the olefin having 5 carbon atoms present in majority amount in the initial hydrocarbon composition.

7. The process according to claim 1, wherein the oligomerization step is conducted in the presence of a catalyst selected from among alumina and aluminosilicates.

8. The process according to claim 1, wherein the catalyst is an aluminosilicate and the $SiO_2/Al_2O_3$ molar ratio of the catalyst ranges from 10 to 80.

9. The process according to claim 1, wherein the catalyst is a mesoporous aluminosilicate having a BET specific surface area greater than or equal to 50 $m^2/g$.

10. The process according to claim 1, wherein the catalyst is an amorphous Si Al catalyst (ASA) with 5 to 95% wt. of silica ($SiO_2$), a BET specific surface area ranging from 100 to 550 $m^2/g$ and accessible pore size ranging from 2 to 14 nm.

11. The process according to claim 1, implemented at a temperature ranging from 80 to 220° C.

12. The process according to claim 1, implemented at a pressure ranging from 2 to 50 bars.

13. The process according to claim 1, further comprising at least one treatment step.

14. The process according to claim 1, comprising a step to recycle an effluent comprising non-reacted C5 olefins.

15. A hydrocarbon fluid capable of being obtained with a process comprising an oligomerization step of an initial hydrocarbon composition comprising at least 2% wt. of 3-methyl-but-1-ene, at least 5% wt. of 2-methyl-but-2-ene and at least 5% wt. of 2-methyl-but-1-ene relative to the total weight of the initial hydrocarbon composition.

16. A process for the formulation of inks, paints, varnishes, cleaning products, lubricants for metal working, dielectric fluids, drilling fluids, cosmetic products, said process comprising using the hydrocarbon fluid according to claim 15 as crude or hydrogenated and/or fractionated solvent cut.

17. The process according to claim 3, wherein the alcohol(s) are selected from fusel oil.

18. The process according to claim 1, further comprising a hydrogenation step and/or fractionation step.

19. The process according to claim 4, wherein the initial hydrocarbon composition comprises at least 50% wt. of branched olefins having 5 carbon atoms selected from among 3-methyl-but-1-ene, 2-methyl-but-2-ene and 2-methyl-but-1-ene, relative to the total weight of the initial composition.

20. The process according to claim 5, wherein the initial hydrocarbon composition comprises at least 50% wt. of 2-methyl-but-2-ene, relative to the total weight of the composition.

* * * * *